United States Patent
Ren et al.

(10) Patent No.: US 9,291,537 B2
(45) Date of Patent: Mar. 22, 2016

(54) LIQUID SALT ENVIRONMENT STRESS-RUPTURE TESTING

(71) Applicant: UT-Battelle, LLC, Oak Ridge, TN (US)

(72) Inventors: Weiju Ren, Knoxville, TN (US); David E. Holcomb, Oak Ridge, TN (US); Govindarajan Muralidharan, Knoxville, TN (US); Dane F. Wilson, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 199 days.

(21) Appl. No.: 14/277,274

(22) Filed: May 14, 2014

(65) Prior Publication Data

US 2015/0330883 A1    Nov. 19, 2015

(51) Int. Cl.
*G01N 3/18* (2006.01)
*G01N 3/08* (2006.01)

(52) U.S. Cl.
CPC ...... *G01N 3/18* (2013.01); *G01N 3/08* (2013.01)

(58) Field of Classification Search
CPC ..... G01N 3/08; G01N 3/18; G01N 2203/0282; G01N 2203/0274
See application file for complete search history.

(56) References Cited

U.S. PATENT DOCUMENTS

| | | | | |
|---|---|---|---|---|
| 3,100,253 A | * | 8/1963 | O'Connor | G01N 3/18 219/201 |
| 3,350,917 A | * | 11/1967 | Wincklhofer | G01N 3/18 374/50 |
| 4,018,080 A | * | 4/1977 | Fletcher et al. | G01N 3/18 374/50 |
| 5,220,824 A | * | 6/1993 | Shelleman | G01N 3/12 374/57 |
| 5,419,201 A | * | 5/1995 | Li | G01N 3/066 324/71.1 |
| 6,026,691 A | * | 2/2000 | Laird | G01N 17/02 73/808 |

OTHER PUBLICATIONS

Ren, Weiju, et al. "Considerations of Alloy N for Fluoride Salt-Cooled High-Temperature Reactor Applications." ASME 2011 Pressure Vessels and Piping Conference. American Society of Mechanical Engineers, 2011. Abstract.*
Ren, Weiju. "Considerations of Alloy 617 Application in the Gen IV Nuclear Reactor Systems: Part II-Metallurgical Property Challenges." ASME 2009 Pressure Vessels and Piping Conference. American Society of Mechanical Engineers, 2009. Abstract.*
Ren, Weiju. "Creep behavior of a continuous strand, swirl mat reinforced polymeric composite in simulated automotive environments for durability investigation: Part I: experimental development and creep-rupture." Materials Science and Engineering: A 334.1 (2002): 312-319.*

(Continued)

*Primary Examiner* — Lisa Caputo
*Assistant Examiner* — Punam Roy
(74) *Attorney, Agent, or Firm* — Klarquist Sparkman, LLP

(57) ABSTRACT

Disclosed herein are systems, devices and methods for stress-rupture testing selected materials within a high-temperature liquid salt environment. Exemplary testing systems include a load train for holding a test specimen within a heated inert gas vessel. A thermal break included in the load train can thermally insulate a load cell positioned along the load train within the inert gas vessel. The test specimen can include a cylindrical gage portion having an internal void filled with a molten salt during stress-rupture testing. The gage portion can have an inner surface area to volume ratio of greater than 20 to maximize the corrosive effect of the molten salt on the specimen material during testing. Also disclosed are methods of making a salt ingot for placement within the test specimen.

20 Claims, 7 Drawing Sheets

(56) References Cited

OTHER PUBLICATIONS

Holcomb, David Eugene, et al. An Analysis of Testing Requirements for Fluoride Salt Cooled High Temperature Reactor Components. Oak Ridge National Laboratory (United States). Funding organisation: NE USDOE-Office of Nuclear Energy (United States), 2009. Abstract.*

Berchmans, L. J., et al. "Stress corrosion cracking and hydrogen embrittlement susceptibility studies on modified 9Cr-1Mo steel weldments in acidic and neutral media." British Corrosion Journal 31.3 (1996): Abstract.*

Stempien, John D. "A Performance Assessment of 316 Stainless Steel in the Fluoride Salt-Cooled High-Temperature Reactor." (2012).*

Sabharwall, Piyush. ASME Material Challenges for Advance Reactor Concepts. No. INL/CON-13-28206. Idaho National Laboratory (INL), 2013.*

McCoy, H. E., et al. "New developments in materials for molten-salt reactors." Nuclear Technology 8.2 (1970): 156-169.*

Whittenberger, J. Daniel. "Tensile properties of HA 230 and HA 188 after 400 and 2500 hour exposures to LiF-22CaF2 and vacuum at 1093 K." Journal of materials engineering 12.3 (1990): 211-226.*

Whittenberger, J. D. "Mechanical properties of haynes® alloy 188 after exposure to LiF-22CaF2, air, and vacuum at 1093 K for periods up to 10,000 hours." Journal of Materials Engineering and Performance 1.4 (1992): 469-482.*

Goods, "Creep and the Corrosion Characteristics of Incoloy Alloy 800 in Molten Nitrate Salts," *J. Materials for Energy Systems*, 3:43-50 (Jun. 1981).

* cited by examiner

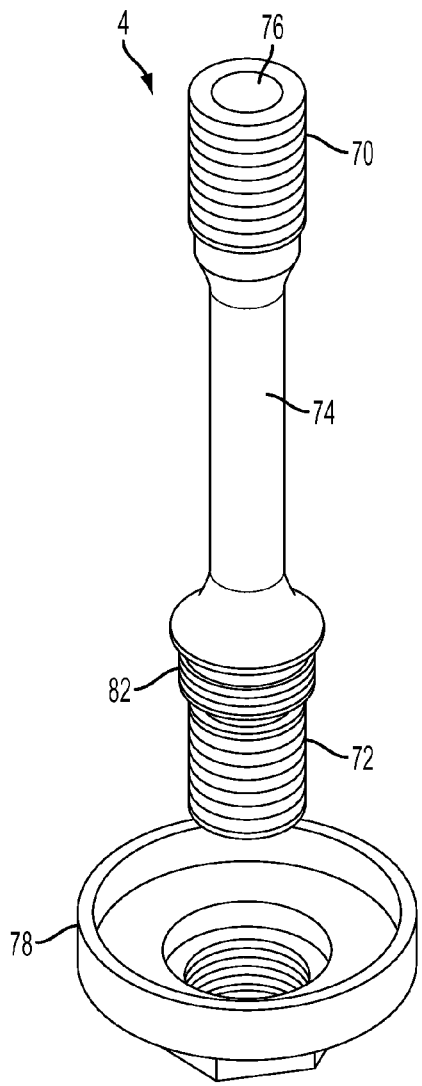
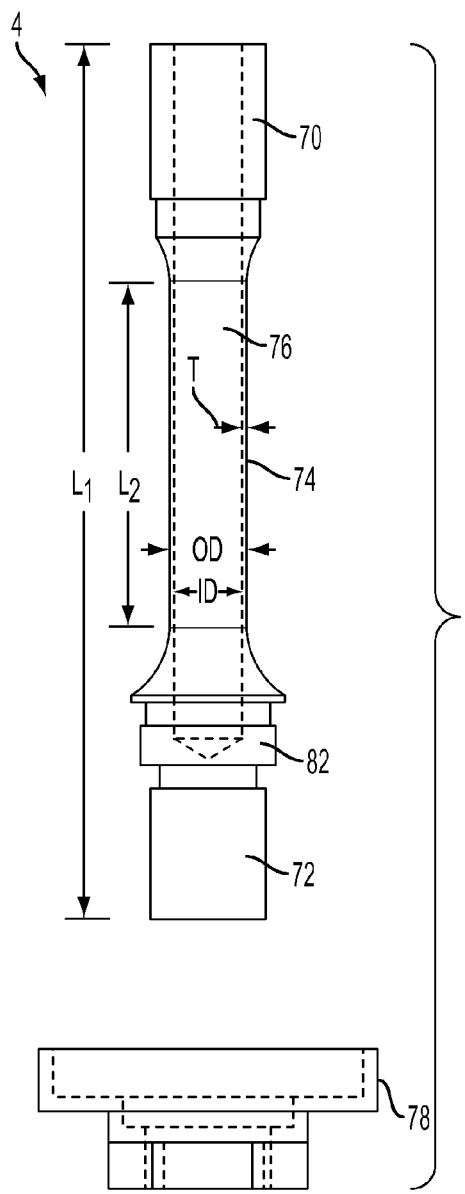
FIG. 5
FIG. 6

LIQUID SALT ENVIRONMENT STRESS-RUPTURE TESTING

ACKNOWLEDGMENT OF GOVERNMENT SUPPORT

This invention was made with government support under Contract No. DE-AC05-00OR22725 awarded by the U.S. Department of Energy. The government has certain rights in this invention.

FIELD

This application is related to stress-rupture testing for applications in high-temperature liquid salt environments.

BACKGROUND

Liquid salts enable efficient, low-pressure heat transfer at high temperatures. No standardly available heat transfer fluids exist with an operational temperature above 600° C. Liquid salt mediums enable higher operating temperatures and thus higher thermodynamic efficiency in high temperature nuclear reactors, solar thermal power systems, and similar systems. Compared to water-cooled reactors, for example, reactors using liquid salt may operate at higher temperatures and thus provide higher thermodynamic efficiency. However, liquid salts can be corrosive to the structural materials necessitating careful material selection and salt chemistry control during operation. Thus, there is a need for systems and methods for testing the ability of heat transfer structural materials to withstand the high temperature, potentially corrosive conditions of liquid salt reactors.

SUMMARY

Disclosed herein are systems, devices and methods related to stress-rupture testing of selected materials within a high-temperature liquid salt environment.

An exemplary system for stress-rupture testing of selected materials in a high-temperature liquid salt environment includes a vertically oriented load train that holds a test specimen in-line and is configured to apply a tension load to the test specimen. The load train is positioned partially within an enclosed vessel that is positioned within or includes a heating mechanism. The vessel can include one or more gas ports for maintaining a controlled inert gas environment within the vessel around the load train, one or more sensor ports, and/or additional access ports for liquid cooling lines and other purposes. The load train can include a first pull rod positioned at least partially within the vessel and extending downwardly from or through the upper end of the vessel, and a second pull rod positioned within the vessel below the first pull rod. The first pull rod has a first specimen grip at a lower end of the first pull rod and the second pull rod has a second specimen grip at an upper end of the second pull rod. The first and second specimen grips are adapted to grip an upper end and a lower end of a test specimen that is being tested. The specimen can include a generally cylindrical tubular gage portion that contains a salt that melts when the testing system is heated to testing temperatures and creates a salt-specimen interface within the gage portion.

Below the heating mechanism, in certain embodiments, the load train includes a thermal break that couples a lower end of the second pull rod and an upper end of a third pull rod, while minimizing heat conduction. In some embodiments, the thermal break can comprise a rigid fixture coupled to the lower end of the second pull rod and a thermally insulating rigid spacer, such as a ceramic disk, supported by the fixture below the second pull rod. The upper end of the third pull rod is supported by the spacer (which is in compression) but is spaced below the lower end of the second pull rod and spaced within the thermal break fixture, such that the third pull rod is thermally decoupled from the second pull rod to reduce heat conduction down the load train into the third pull rod.

This is advantageous because it allows for a load cell to be placed in the third pull rod to measure the load applied to the test specimen. The load cell can be shielded from the high-temperatures higher up the load train, which would otherwise damage the load cell. This allows the load cell to be placed within the vessel instead of being located below the vessel. The third pull rod can have a lower end below the load cell that extends through a lower end of the vessel and is adapted to be coupled to a loading source for applying a load to the test specimen via the second and third pull rods and the thermal break. Friction can occur between the third pull rod and the lower end of the vessel which can distort the amount of load applied to the test specimen compared to the actual load applied outside of the vessel. Thus, locating the load cell within the vessel eliminates such distortion and provides a more accurate load measurement.

In some embodiments, a gap is provided between the third pull rod and the lower opening of the vessel such that an inert process gas from within the vessel is allowed to exit the vessel through the gap during testing. This gap also provides a minimization of friction. Additional low-friction bearings or rings can be included at the interface to keep the gap consistent and allow load transfer with minimal interference by friction.

The system can be configured to apply a tension load to the gage portion of the test specimen while the test specimen is maintained at use temperatures wherein the salt is molten, such as at a temperature that is at least 100° C. greater than the melting temperature of the salt, such as greater than 700° C. for example. Exemplary salts can comprise $2^7LiF$—$BeF_2$ and the low melt point eutectic of $KF$—$ZrF_4$.

An exemplary test specimen disclosed herein includes a first end portion having a first engagement portion for connecting to a stress-rupture testing system, a second end portion having a second engagement portion for connecting to the stress-rupture testing system, a narrowed gage portion between the first and second end portions, and an inner void extending through the first end portion and through the gage portion. The gage portion has a substantially cylindrical outer surface defining an outer diameter and the inner void is substantially cylindrical within the gage portion such that the gage portion has a substantially cylindrical inner surface defining an inner diameter and the gage portion has a substantially constant wall thickness between the inner diameter and the outer diameter. The inner void is configured to receive a solid salt ingot or powdered salt such that when the test specimen is subjected to high temperatures, the salt melts to form molten salt that completely fills the portion of the void that is within the gage portion.

In some embodiments, a ratio $Ai/V$ of the gage portion is at least about 20, or from about 20 to about 32, wherein $Ai$ is the inner surface area of the gage portion and $V$ is the volume of test specimen material (e.g., a metal alloy) in the tubular gage portion between the inner surface of the gage portion and the outer surface of the gage portion, in units of square inches divided by cubic inches.

In some embodiments, a basin ring is attached around the test specimen below the gage portion and configured to catch the liquid salt that escapes from inside the test specimen when the test specimen ruptures and leaks during stress-rupture testing.

Exemplary methods of stress-rupture testing of a material in a high-temperature liquid salt environment can include creating a solid salt ingot (or salt powder), placing the salt ingot (or salt powder) within an inner void of a test specimen and sealing the void closed, mounting the test specimen with the salt ingot enclosed in a load train within a vessel of a stress-rupture testing system, filling the vessel with an inert gas, heating the test specimen while mounted in the load train within the vessel filled with inert gas such that the salt ingot melts within the void and the resulting molten salt contacts an entire inner surface of a gage portion of the test specimen, applying and sustaining a load on the gage portion of the test specimen while the test specimen is mounted in the load train within the vessel filled with inert gas and the salt is molten, and measuring the applied load, time elapsed, gage portion elongation, and/or other parameters until the gage portion of the test specimen fails. The inert gas can be continuously fed into the vessel while the load is applied and a small quantity of inert gas is allowed to escape from the vessel through the gap between the load train and a lower end of the vessel to ensure no air ingress occurs.

Exemplary methods for forming a salt ingot for use in the stress-rupture testing system can include: placing a mold within a vacuum chamber, creating an inert gas environment within the vacuum chamber around the mold, heating the mold within the vacuum chamber in the inert environment to remove impurities from the mold, placing a salt into the mold and closing the mold in an inert environment, heating the mold to remove impurities such as moisture and oxygen, melting the salt to remove voids from the salt, cooling the mold to solidify the salt into a salt ingot with impurities removed, and transferring the salt ingot from the mold into a test specimen in an inert environment. Creating an inert gas environment within the vacuum chamber can comprise drawing a vacuum on the vacuum chamber and feeding an inert gas into the vacuum chamber to flush out ambient air from the vacuum chamber. The method can further comprise: placing a funnel and a mold housing within a vacuum chamber along with the mold; heating the mold, funnel, and mold housing within the vacuum chamber in the inert environment to remove impurities from the mold, funnel, and mold housing; transporting the mold and funnel sealed within the mold housing from the vacuum chamber to a salt-filling chamber having an inert environment; using the funnel to place purified salt into the mold in the salt-filling chamber; and/or transporting the salt-filled mold sealed within the mold housing from the salt-filling chamber to a vacuum chamber.

The foregoing and other objects, features, and advantages of the disclosed technology will become more apparent from the following detailed description, which proceeds with reference to the accompanying figures.

BRIEF DESCRIPTION OF THE DRAWINGS

FIG. 5 is a perspective view of an exemplary test specimen used in the system of FIG. 1.

FIG. 6 is a side view of the test specimen of FIG. 5.

DETAILED DESCRIPTION

Figure 1:
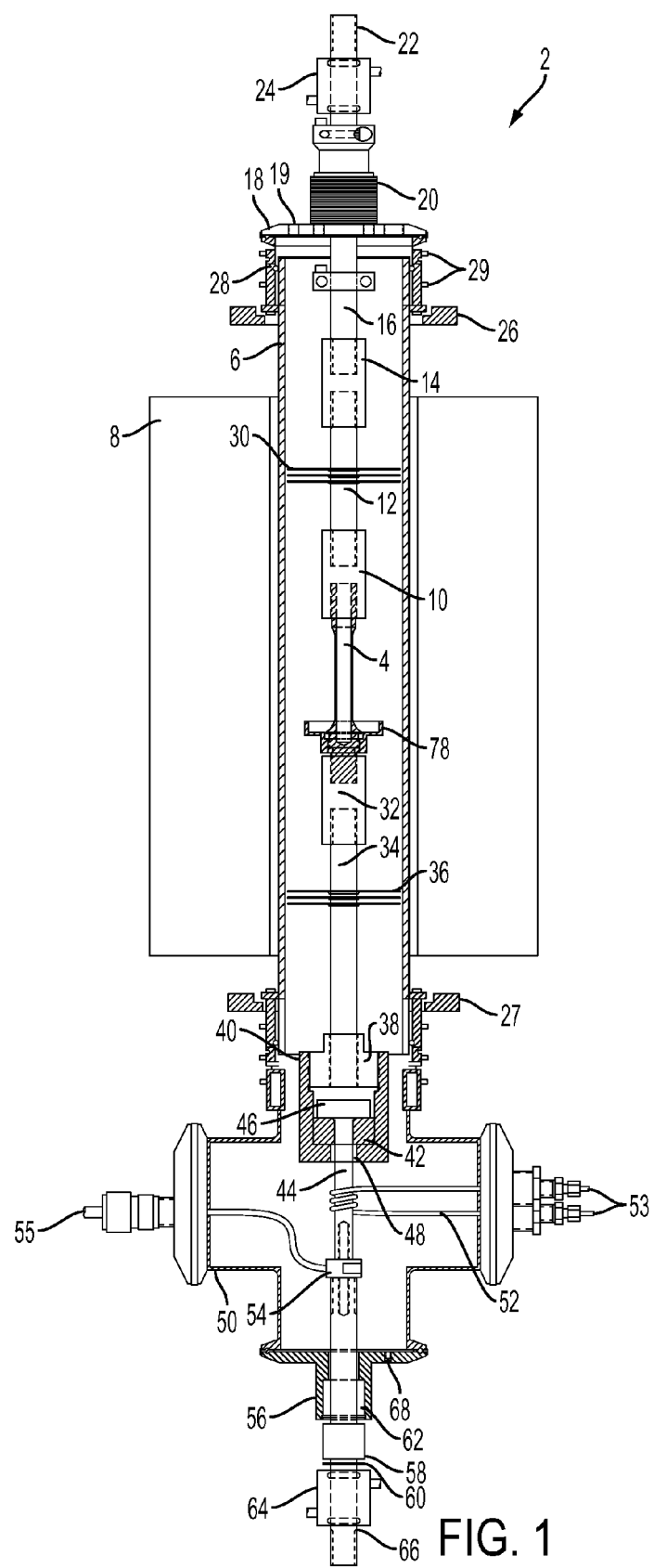
FIG. 1 is a partially cross-sectional side view of an exemplary testing system disclosed herein.

Disclosed herein are devices, systems and methods for testing the ability of materials to withstand applied stress while being exposed to high-temperature and corrosive environments that simulate conditions within a liquid salt heat transfer/heat storage system, such as within liquid salt nuclear reactors or solar thermal power systems. For example, large solar panel arrays can generate a great amount of heat during the day, and that heat can be stored using a liquid salt heat storage system during the day and then utilized to continue generating power during the night when the solar panels are not producing power.

In an exemplary testing procedure, a test specimen is formed of a material of interest (e.g., a metal alloy) and the test specimen is placed under load while in contact with a liquid salt (also referred to as molten salt) and at high temperatures. The test specimen's ability to withstand the applied load under such conditions is measured, such as to characterize how well the material of interest is likely to perform if used in a liquid salt heat transfer system.

The disclosed testing systems can provide one or more advantages that allow for accurate testing of material performance in the harsh conditions of a liquid salt nuclear reactor or liquid salt heat exchanger. For example, some disclosed testing systems are able to function at very high temperatures, such as at least 700° C., a range of from 700° C. to 1000° C., or even greater than 1000° C., which can simulate the operating temperatures of modern and future liquid salt reactors. For example, in some embodiments, the testing system can heat the test specimen to a temperature that is at least 100° C. greater than the melting temperature of the salt. Also, certain embodiments of the disclosed testing systems are able to safely contain and apply corrosive salts, such as $2^7$LiF—$BeF_2$, KF—$ZrF_4$, other fluoride containing salts, and the like, at such high temperatures, while minimizing contamination of the salts, in solid and liquid phases, before and during the preparation and testing procedures. In addition, certain embodiments of the disclosed testing systems are configured to provide enough liquid salt in contact with the test specimen material to adequately test the materials resistance to the corrosive effects of the liquid salt while under stress, while minimizing exposure of the test material to undesired influences, such as oxygen and moisture from atmospheric air. Further, the load train and specimen holders of certain of the disclosed testing systems are constructed to provide high stress-rupture strength at such very high temperatures, and are desirably protected from the corrosive liquid salts that are in contact with the test specimen during testing. Furthermore, disclosed systems can include mechanisms to accurately control and measure the loads that are applied to the test specimen during testing, while being protected from the high-temperature, corrosive testing environment. Many other advantages and benefits can also be provided by the disclosed systems and methods.

Figure 2:
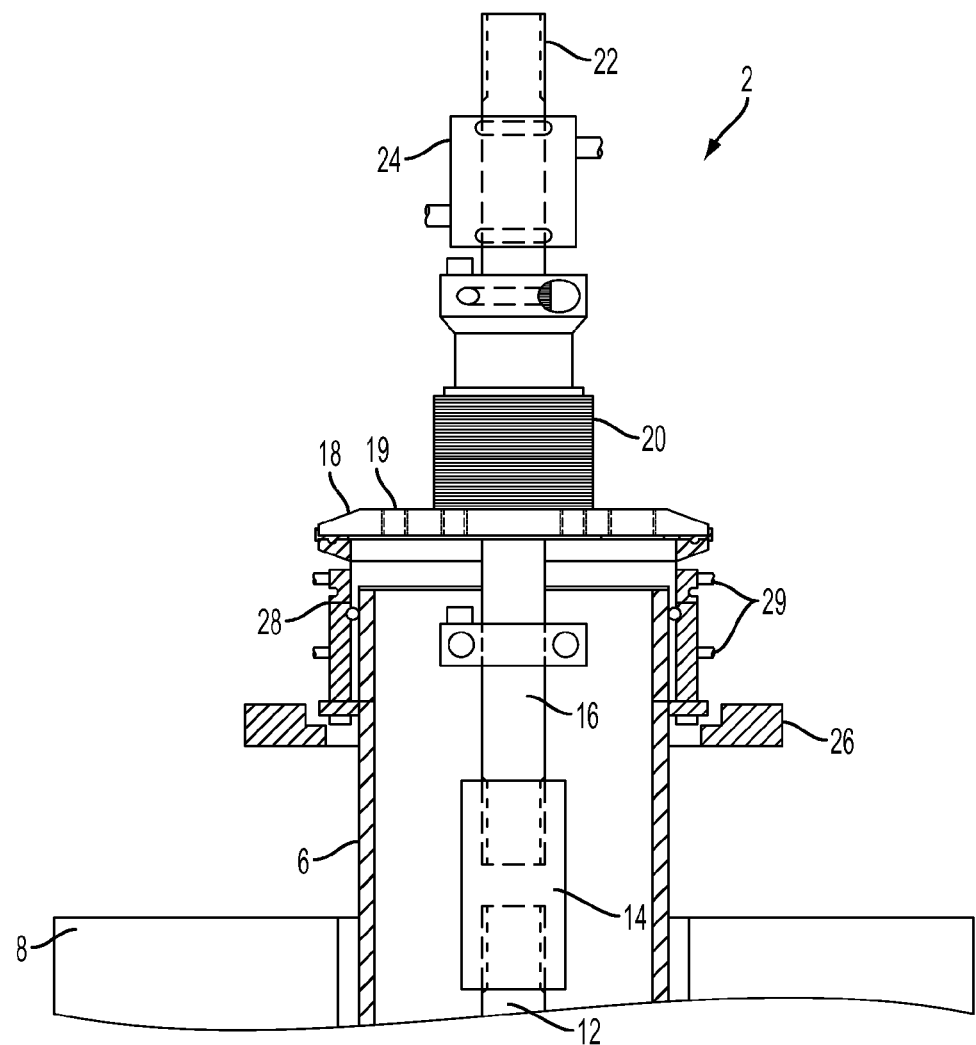
FIG. 2 shows an upper portion of the system of FIG. 1.
Figure 3:
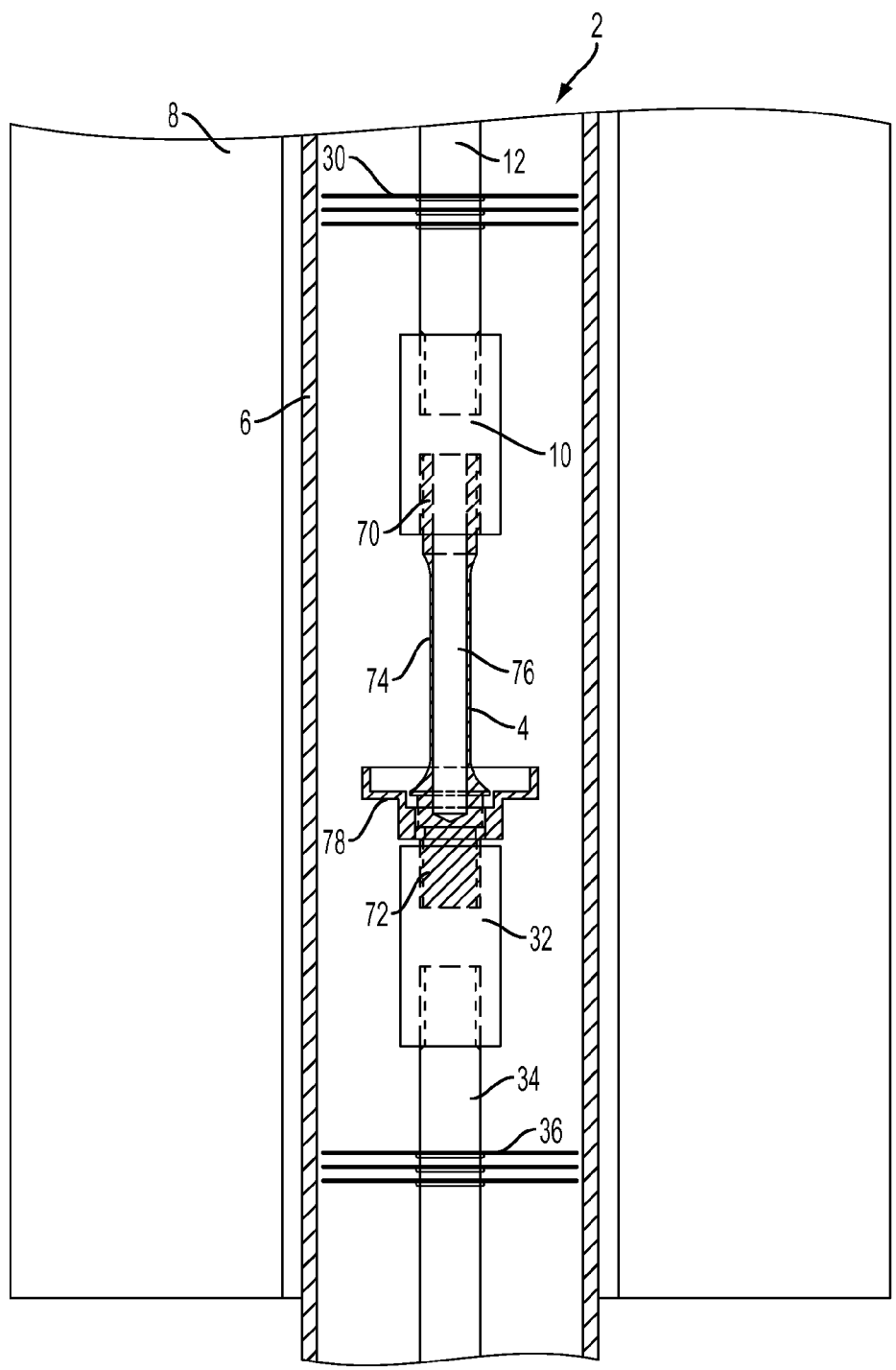
FIG. 3 shows an intermediate portion of the system of FIG. 1.
Figure 4:
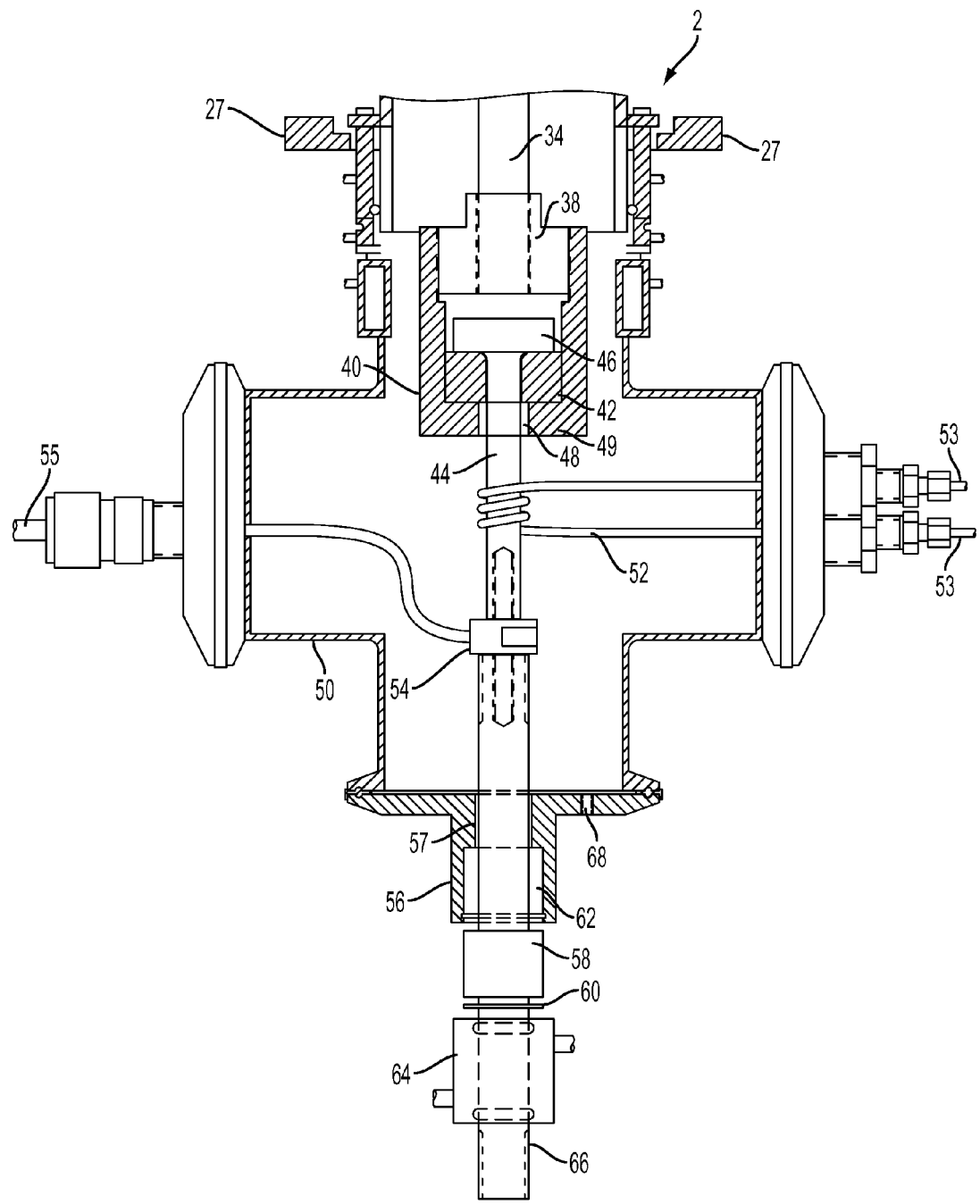
FIG. 4 shows a lower portion of the system of FIG. 1.

FIG. 1 shows an exemplary testing system 2 for testing a test specimen 4 in an environment simulating a liquid salt nuclear reactor or liquid salt heat exchanger. FIGS. 2-4 show enlarged views of different portions of the system 2, and FIGS. 5 and 6 show detailed views of the test specimen 4.

As shown in FIG. 1, the test specimen 4 is held in a substantially vertical orientation in a load train of the testing system 2 and positioned within an elongated vessel 6. In other embodiments, the load train can be oriented non-vertically, such as horizontally or at other angles from vertical. The illustrated embodiment is oriented vertically to utilize gravitational forces to apply constant tension to the test specimen and ensure that the liquid salt fills the gage portion of the specimen during testing. However, in other embodiments other mechanisms can be used to apply tension to the test specimen while the specimen is at a non-vertical orientation, while maintaining sufficient surface contact of the liquid salt against the specimen material.

The vessel 6 is used to provide a controlled environment around the test specimen and the load train during testing. For example, the vessel 6 can be filled with an inert gas, such as argon, during testing to protect the load train components and the test specimen from oxidizing or otherwise reacting to the ambient environment in the vessel at high temperatures. For example, in some embodiments, load train components can comprise titanium-zirconium-molybdenum alloy (TZM), which can be susceptible to reaction with oxygen and other elements in atmospheric air at high testing temperatures. The vessel 6 can also be constructed of a non-reactive material, such as alumina. The vessel 6 can be supported independently from the load train, such as by mounting brackets 26 and 27. The system 2 also includes a heating mechanism, such as the furnace 8, adjacent to the vessel 6 for maintaining the test specimen and salts at a desired temperature during testing.

The load train can comprise an aligned series of components that hold the test specimen 4 within the testing system 2 and apply desired loads to the test specimen during testing. The load train can comprise upper components that couple the test specimen 4 to a stationary upper mounting location and lower components that couple the test specimen to a loading source (not shown) below the system 2. When a load is applied by the load train during testing, a gage portion 74 of the test specimen 4 (see FIGS. 5 and 6), which is exposed to the liquid salt, is stressed to determine the test specimen material's ability to withstand the environmental rigors of a liquid salt nuclear reactor. The data are then used to characterize the material being tested.

As shown in the illustrated embodiment, for example, the upper part of the load train (see FIGS. 2 and 3) can include couplings 10, 14 and pull rods 12, 16 that couple an upper end of the test specimen 4 to a stationary upper support (not shown) via a threaded upper end 22 of the pull rod 16. The upper portion of the load train extends through an opening at the upper end 18 of the vessel 6, which can be sealed, such as with a bellows-type seal 20, to prevent inert gas from escaping or atmospheric gas from entering the vessel.

The system 2 can include thermal shields 30, 36 mounted on the load train above and below the test specimen 4. The shields 30, 36 reduce convection and radiation heat loss from the testing zone where the specimen gage section locates to facilitate maintaining a uniform temperature gradient within the testing zone and minimizing heat outside the testing zone. The shields 30, 36 can be spaced slightly from the inner walls of the vessel 6 to avoid frictional forces on the load train that can disrupt the testing procedure.

As shown in FIGS. 3 and 4, the lower part of the load train couples the lower end of the test specimen to the loading source. A lower end of the load train extends through a seal assembly 56 at the lower end of the lower chamber 50 of the vessel 6 and includes a threaded lower end 66 that is configured to attach to the loading source below the testing system 2. The loading source can be a dead weight hanging from the load train, or other loading mechanisms known in the art. The lower part of the load train can include a thermal break between the components that are coupled to the lower end of the test specimen 4 within the furnace 8 (e.g., coupling 32 and pull rod 34), and the lower components of the load train (e.g., lower pull rod 44) that are coupled to the load source. The thermal break significantly limits heat conduction downwardly through the load train, which protects temperature sensitive components below the thermal break.

For example, a load cell 54 that is vulnerable to high temperatures can be attached to, or be inserted between upper and lower portions of, the lower pull rod 44 below the thermal break for measuring the amount of load applied to the test specimen. The load cell 54 can be electrically coupled to data collection systems outside the system 2 via connection 55. Placement of the load cell 54 within the vessel 6 allows for more accurate measurement of the load that is applied to the test specimen 4 as it accounts for frictional influence between the lower pull rod 44 and the seal assembly 56 of the vessel. Placement of the load cell 54 within the vessel 6 is enabled by use of the thermal break. The load cell 54 can be threadably inserted between an upper portion of the lower pull rod 44 and a lower portion of the lower pull rod, such that the load cell can measure the total amount of force that is transmitted along the lower pull rod 44.

The thermal break (see FIG. 4) provides a break in the thermal conduction pathway downward through the load train. The pull rods (e.g., 34, 44) and couplings (e.g., 32) of the load train can comprise a metal material that maintains high strength at very high testing temperatures, such as TZM. Unlike other common metals, TZM load train components remain very strong and provide sufficient strength to the specimen grips and other load train connections during the high temperature conditions during testing. However, TZM and other high-temperature-resistant metals can also be good thermal conductors. The thermal break includes thermally insulating material, such as ceramic materials, such that the pull rod 34 above the thermal break is thermally insulated from the lower pull rod 44 below the thermal break.

In the embodiment of FIG. 4, thermal break includes a thermal break adaptor 38, a thermal break fixture 40, and an insulating spacer 42. The adaptor 38 and fixture 40 can comprise metal materials that are strong in tension, like the TZM pull rods 34 and 44. The adaptor 38 can be threadably attached to the lower end of the pull rod 34, and the fixture 40 can be threadably attached around the adaptor 38. The insulating spacer 42 can comprise a ceramic disk, for example, that rests on a lower ledge 49 of the fixture 40 and supports an upper rim or head 46 of the pull rod 44. The pull rod 44 passes through a lower opening 48 in the fixture 40 without contacting the fixture to prevent direct thermal conduction from the fixture 40 to the pull rod 44. The upper head 46 of the pull rod 44 is flared radially such that the upper head forms a lower contact surface that rests on top of the spacer 42. The spacer 42 can fit tightly around pull rod 44 under the head 46 to restrain the pull rod 44 from moving radially relative to the spacer, and the spacer 42 can also fit tightly within the fixture 40 to restrain the spacer from moving radially relative to the fixture. A ceramic material of the spacer 42 can provide high strength in compression between the pull rod head 46 and the lower ledge 49 of the fixture 40, while also providing thermal insulation. Furthermore, the upper surface of the pull rod head 46 is spaced from the lower surfaces of the pull rod 34 and adapter 38, and spaced radially from the inner surfaces of the fixture 40 to minimize thermal conduction. The adapter 38 can be removed from the fixture 40 to provide access for inserting the spacer 42 and the pull rod 44 into the fixture. The fixture 40 can comprise a generally cylindrical or tubular configuration or can have other suitable configurations.

The vessel 6 can comprise a lower chamber 50 below the furnace, such as a cross-chamber having lateral access ports. The lower chamber can include a cooling system 52 and related ports 53 for cooling the lower end of the load train, such as a fluid that flows through a coil wrapped around the pull rod 44 below the thermal break. The load cell 54 can be positioned below the coil of the cooling system 52 such that the load cell is further protected from thermal damage. In addition to the thermal break and the cooling system 52, the various components of the testing system 2 can include additional cooling systems to dissipate heat. For example, the vessel 6 can include fluid ports 29 (see FIG. 2) and the lower chamber 50 can also include fluid ports for circulating a cooling fluid, such as water. In addition, the upper pull rod 16 and lower pull rod 44 can include fluid-cooled adapters 24 and 64, respectively, for circulating cooling fluid around and/or through the pull rods. In some embodiments, the pull rods can include one or more hollow passageways extending through the pull rods for circulating cooling fluid.

As shown in FIG. 4, the lower end of the vessel includes a seal assembly 56 that allows the pull rod 44 to pass through the lower end of the vessel with minimal frictional resistance to relative vertical motion. A small gap 57 is allowed between the pull rod 44 and the inner walls of an opening passing through the seal assembly 56 such that the pull rod 44 does not contact the inner walls of the seal assembly. A bushing 58 and/or a ring 60 can be positioned around the pull rod 44 and can fit securely within a lower recess 62 of the seal assembly below the gap 57 to keep the pull rod centered in the lower opening and maintain the small gap 57, while allowing the pull rod to slide vertically relative to the vessel with minimal friction. The bushing 58 and/or ring 60 can be made of a material that has a very low coefficient of friction with the pull rod 44. The bushing 58 and/or ring 60 can include one or more vertical holes, such as drilled holes, to further facilitate the escape of inert gas through the gap 57.

The vessel 6 can include one or more process gas inlets, such as inlet 68 in the lower end seal assembly 56 (FIG. 4) and/or an inlet in the upper end 18 of the vessel (not shown), which allow an inert process gas, such as argon, to be fed into the vessel. The process gas can escape through the gap 57 and/or through other outlets, such as an upper outlet at the top end of the vessel, while additional process gas can be fed into the vessel through one or more inlets, such as the inlet 68, to maintain a positive flow out of the vessel 6, which inhibits unwanted external gases from entering the vessel. During set up of the system, atmospheric air captured within the vessel 6 can initially be purged out through an upper gas outlet near the top end of the vessel (since the process gas is heavier than air) by feeding in the process gas through one or more inlets, such as lower inlet 68, for a sufficient period of time. Other ports can also be provided in the vessel 6, such as ports 19 (FIG. 2) for thermocouples that attach to the test specimen, a salt leak indicator attached to a basin ring 78 (FIG. 3), and ports for other sensors and wiring.

FIGS. 5 and 6 show an embodiment of a test specimen 4 and the basin ring 78 that is attached around a lower threaded portion 82 of the test specimen 4 for catching liquid salt that escapes from the test specimen when it ruptures or leaks during testing.

The test specimen 4 includes an upper connector 70, a lower connector 72, and a gage portion 74 between the upper and lower connectors. The connectors 70 and 72 are threaded to attach to upper and lower couplings 10 and 32, respectively, of the load train. The couplings 10 and 32 are also referred to as grips. The threaded upper and lower connectors 70, 72 are sized such that they are stronger in tension than the gage portion 74, such that stress-rupture failure occurs first in the gage portion. The test specimen 4 includes an inner void 76 that extends through the gage section and the upper connector 70. The void 76 is open at the upper end of the upper connector for loading the salt and then closed off prior to testing (e.g., immediately after loading the salt) to ensure containment of the liquid salt during testing and to protect the salt from contamination. The void 76 is configured to be welded closed, for example, to contain the salt in its corrosive liquid phase during testing at high temperatures.

The test specimen 4 can have an overall longitudinal length $L_1$ of about 5.67 inches (144 mm) and the gage portion 74 can have a longitudinal length $L_2$ of about 2.25 inches (57.2 mm), though the lengths $L_1$ and $L_2$ can vary in other embodiments. The gage portion 74 can be substantially cylindrical. The gage portion 74 can have a nominal outer diameter OD of about 0.50 inches (12.7 mm), while the OD can vary in other embodiments. The inner diameter ID of the gage portion 74 (e.g., the diameter of the inner void 76) and the radial wall thickness T of the gage portion 74 can be selected based on various factors. With an OD of about 0.50 inches, for example, the ID can be selected from a range of from about 0.41 inches (10.414 mm) to about 0.44 inches (11.176 mm).

The deleterious effects of the liquid salt on the load bearing properties of the metal of the gage portion 74 increase as the salt-metal contact area (e.g., the inner surface area of the gage portion) increases, and the deleterious effects of the liquid salt on the load bearing properties of the metal of the gage portion decrease as the total volume of metal in the gage portion increases. Thus, the liquid salt's effect on the load bearing properties of the metal of the gage portion 74 is generally proportional to the ratio of Ai/V, where Ai is the salt-metal contact area in the gage portion and V is the volume of metal in the gage portion. For a cylindrical gage portion, the ratio Ai/V can be equal to $4 \cdot ID/(OD^2 - ID^2)$. Increasing the inner diameter ID, and thereby decreasing the thickness T, has the effect of increasing Ai and decreasing V, thereby increasing the Ai/V ratio and increasing the effect of the salt on the strength of the metal. Increasing the Ai/V ratio is generally desirable for providing more significant observable effects of the salt on the metal. For example, an Ai/V ratio (in unit of square inches/cubic inches) greater than 2, greater than 10, and/or greater than 20 can be achieved. The dimension ranges provided above result in an Ai/V ratio (in unit of square inches/cubic inches) of from about 20 to about 32.

However, if the wall thickness T is too small, the total load bearing capacity of the gage portion 74 can become so small that loading error tolerances become too significant. Furthermore, manufacturing tolerance limitations can restrict how small the wall thickness T can be while providing accurate testing conditions. For example, with an OD of about 0.50 inches, a minimum wall thickness T can be about 0.06 inches.

It can be desirable to compare the performance of the disclosed test specimen to the performance of a solid test specimen that has its outer surface exposed to atmospheric air, and is not exposed to salt, during testing. Such a comparison can help determine how significant the effects of the liquid salt are on the test specimen material. However, for a more accurate comparison, it can be desirable to have the solid specimen and the liquid salt specimen have the same or similar Ai/V ratios. In a solid specimen, Ai is the outer air-metal contact area and V is the total volume of metal. In the exemplary liquid salt test specimens described above with an OD of about 0.5 inches and an ID selected from a range of about 0.41 inches to about 0.44 inches, the resulting Ai/V ratio range (in unit of square inches/cubic inches) of from about 20 to about 32 can be about equal to the Ai/V ratio range for a comparative solid test specimen having an OD of from about 0.125 inches (3.175 mm) to about 0.2 inches (5.08 mm), which corresponds to the dimensions of common solid specimen types for which ample test data is available for comparison to data collected from the herein described liquid salt environment testing techniques.

The inner void 76 of the test specimen 4 contains the liquid salt during testing such that the entire gage length $L_2$ of the void is filled with the liquid salt and the upper level of the liquid salt is within the upper connector 70. This ensures that the entire inner surface area of the gage portion 74 remain in contact with the liquid salt during testing. However, it can be challenging to get the salt into the void 76 and seal the salt within the void while minimizing the amount of contaminants that become trapped in the void 76 as well. Most applicable salts are in solid phase below about 400° C., so they are in the solid phase when the salt is placed into the void 76 at room temperature, and thus it can be difficult to avoid trapping air, moisture, and/or other contaminants in the void 76 along with the solid salts. For example, the salts can easily oxidize or adsorb oxygen and moisture if exposed to air or moisture, in either the solid or liquid phase. Trapped oxygen, moisture and other oxidizers within the specimen void can react with the test specimen material, especially at high temperatures.

To minimize contamination and oxidation of the salt, the salt can be initially placed into a mold in a granular or chunk form and then heated and melted in an very low oxygen and moisture environment to minimize impurities such as oxygen, moisture, and other gases from the surface of the salt particles and within the voids between the salt particles and to form a solid ingot having dimensions to completely fill the void within the test specimen. The heated formation of the ingot can remove moisture, air, and other contaminants from the salt and produce a salt ingot with substantially reduced contaminants; and because the ingot fills the void 76, the air and moisture in the void is forced out when the ingot is inserted into the void and sealed closed, such that reactions of the internal surface of the test specimen with contaminants such as oxygen and moisture is minimized.

The salt ingot preparation procedure can be performed in a vacuum or other environments of very low oxygen and very low moisture content, which minimizes exposure of the salt to air and moisture. Salt, particularly in a powdered form, readily adsorbs oxygen and moisture from the air, which can cause corrosion and/or oxidation when the salt is placed in the specimen and heated. Preparing the salt in a vacuum addresses that problem.

The use of a solid salt ingot can also help to ensure that the gage portion of the test specimen 4 is completely filled with liquid salt during testing. When the solid ingot melts, its upper surface level does not change significantly from the solid phase to the liquid phase because there is minimal void space within the ingot and between the ingot and the internal surface of the test specimen. However, when a powdered salt is placed directly into the specimen, the upper surface level of the salt can drop significantly when the salt melts and the gas trapped in the voids of the powder vaporizes and rises to the top of the salt. Thus, a sufficient volume of powder must be added into the test specimen so that the upper surface level remains above the gage portion after the salt melts.

Exemplary Salt Ingot Preparation System

Figure 7:
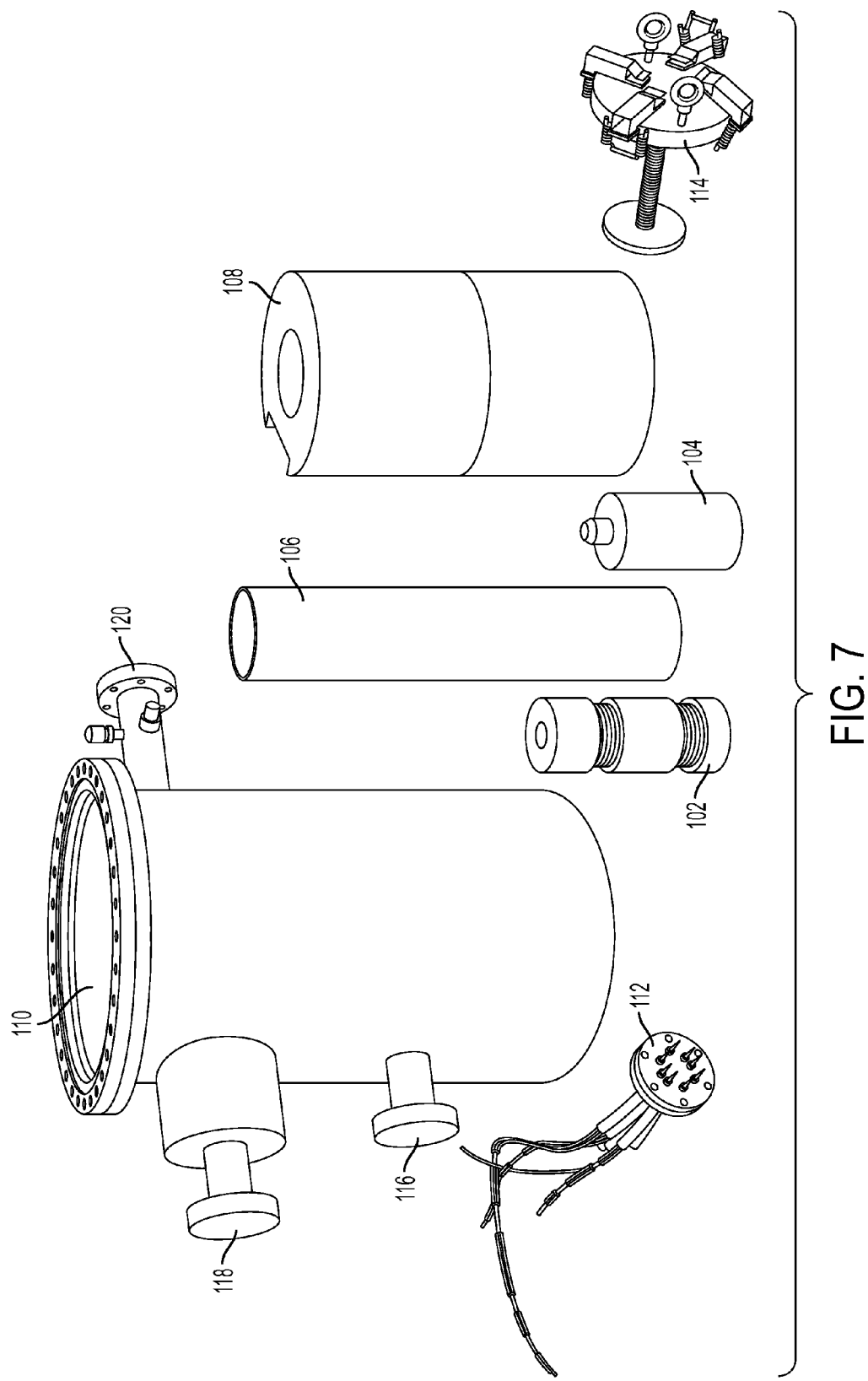
FIG. 7 shows various exemplary components of a salt ingot preparation system.
Figure 8:
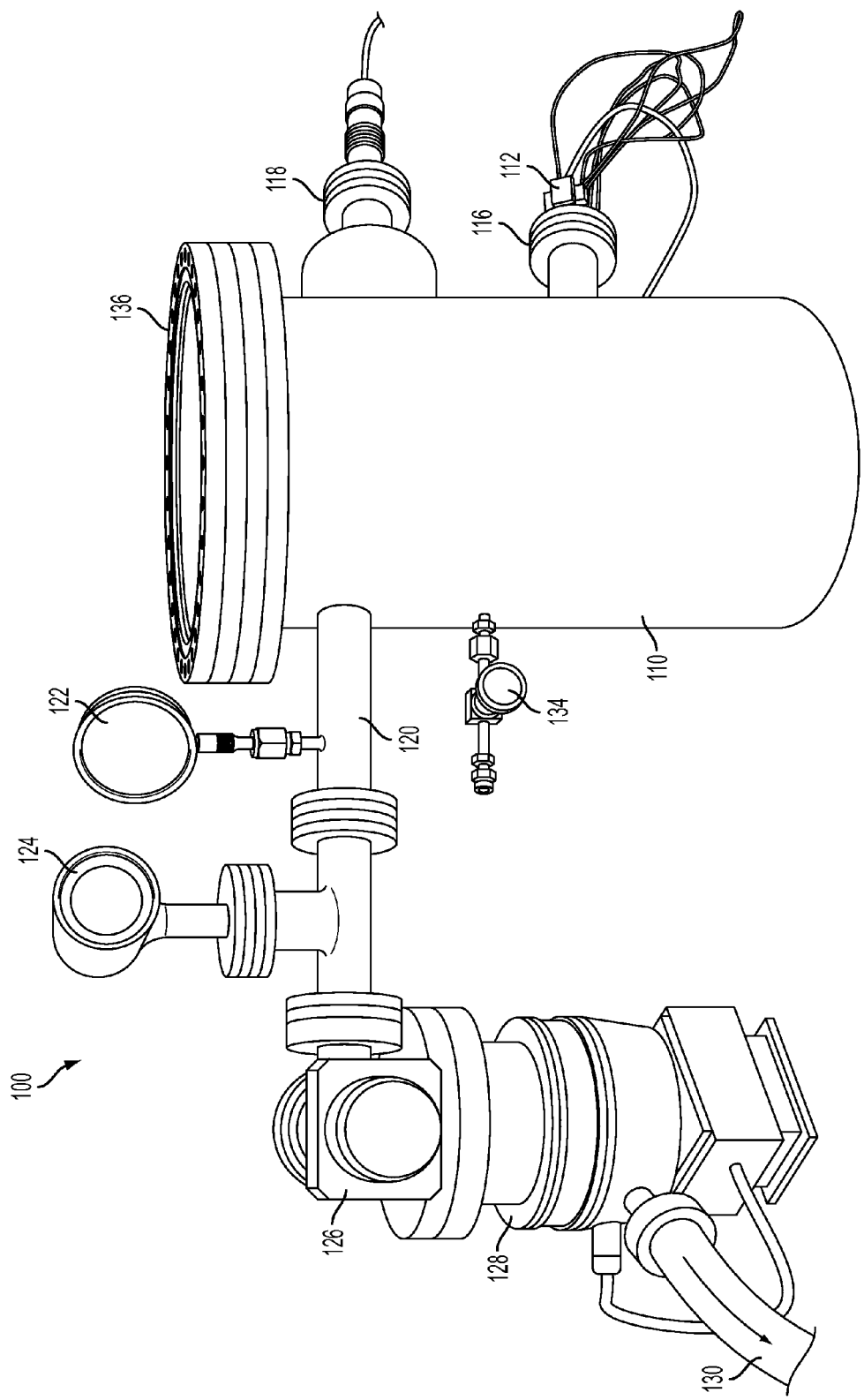
FIG. 8 shows an exemplary salt ingot preparation system.

FIGS. 7 and 8 illustrate an exemplary salt ingot preparation system 100 for creating a salt ingot for use in the herein described testing systems. FIG. 7 shows certain components of the salt ingot preparation system 100 individually, and FIG. 8 shows the system 100 assembled.

As shown in FIGS. 7 and 8, the system 100 can comprise an ingot mold 102 (e.g., made of graphite), a funnel 104 (e.g., made of graphite), a mold housing 106, a furnace 108, a vacuum chamber 110, a thermocouple attachment 112, and a quick release seal 114 for the mold housing. The funnel 104 is configured to be placed on top of the mold 102 to allow solid salt to be poured into the mold. The mold 102 and funnel 104 are configured to be positioned within the mold housing 106. As illustrated, the mold housing 106 is missing a clamp ring for the quick release seal 114. The quick release seal 114 as illustrated is also missing an axial spring that is positioned along the shaft of the quick release seal. The quick release seal 114 is configured to be positioned over the mold housing 106 and seal the mold and funnel within the mold housing. The furnace 108 is configured to be positioned within the vacuum chamber 110 and the mold housing 106 is configured to be positioned within the furnace. The thermocouple attachment is configured to be attached to a port 116 of the vacuum chamber 110, as shown in FIG. 8. The vacuum chamber 110 can also include an electrical power port 118 for connecting power to the furnace 108 (FIG. 8), a vacuum port 120, a gas port 134, and an upper member 136 (with an optional optical window) that seals off the top of the chamber 110 (FIG. 8).

FIG. 8 shows the assembled vacuum chamber 110 in a sealed state, optionally with one or more of the furnace 108, mold housing 106, mold housing clamp ring, funnel 104, mold 102, and the salt sealed within the chamber. An electrical power supply is attached to the electrical power port 118 to power the furnace, the thermocouple attachment 112 is attached to the port 116 to monitor the temperature of the furnace within the chamber 110, a valved gas line is attached to the gas port 134, and a vacuum pump 128 is attached to the vacuum port 120. A low vacuum gauge 122 and a high vacuum gauge 124 can also be attached to the vacuum line 120 to monitor the vacuum level. A vacuum valve 126 is positioned between the vacuum pump 128 and the vacuum line 120 into the chamber 110. The vacuum pump 128 can comprise a turbomolecular vacuum pump, for example. In some embodiments, an outlet line 130 from the vacuum pump 128 is coupled to a roughing vacuum pump (not shown), such as for a turbomolecular vacuum pump. The gas line attached to the gas port 134 can be coupled to a supply of a process gas, such as Argon-4% Hydrogen (Ar-4% H2), which is pumped into the vacuum chamber to replace the ambient air and minimize contamination and corrosion and/or oxidation.

In an alternative embodiment, the furnace or other heat source can be located outside of the vacuum chamber. As such, the vacuum chamber can have a smaller volume. The smaller volume within the vacuum chamber can reduce the time needed to achieve the desired vacuum level within the chamber and/or can increase the time needed to achieve the melting temperature.

Exemplary Salt Ingot Preparation Procedures

The following describes an exemplary procedure for preparing a salt ingot and installing the salt ingot into a test specimen for use in the testing systems described herein.

In an initial "bake-out" phase, oxygen, moisture and other impurities are removed from the equipment used to make the salt ingot. Oxygen and moisture in combination with molten salts, such as molten fluoride salts can cause increased corrosion of alloys. The bake-out phase can include all or some of the following steps:

1. Install funnel, mold, and mold housing into vacuum chamber centered within furnace.
2. Attach connections and flanges on vacuum chamber and seal vacuum chamber.
3. Pull high vacuum on vacuum chamber.
4. Back fill vacuum chamber with Ar-4% H2.
5. Optionally repeat steps 3 and 4 as needed. Target vacuum is greater than $10^{-6}$ torr.
6. In high vacuum, heat with furnace to 850° C.
7. Hold at temperature over 48 hours for first use, 6 hours for subsequent batches.
8. Cool down in high vacuum.

In a subsequent "salt fill" stage, the salt is placed in the mold and sealed without exposing the salt to air or moisture. The salt fill stage can include all or some of the following steps:

9. Start Ar-4% H2 flow.
10. With Ar-4% H2 flowing, open vacuum chamber.
11. With Ar-4% H2 flowing, quickly place a mold housing seal onto mold housing and clamp closed.
12. With Ar-4% H2 flowing, remove mold housing from vacuum chamber.
13. With Ar-4% H2 flowing, reseal vacuum chamber.
14. Transport sealed mold housing to a glove box with very low oxygen and very low moisture content, such as via an anti-chamber. Steps 9-14 allow for mold and funnel to be transported into the glove box with minimal exposure to air and moisture.
15. In glove box, weigh out the appropriate amount of previously purified salt (e.g., as irregularly shaped chunks). In the case of fluoride salts, purification steps include removal of adsorbed oxygen and moisture, hydrofluorination of the melted salt to remove additional impurities such as oxides and sulfur compounds, flushing of the process gases, and filtration of the melted salt. Post-purification, the salt can be maintained in very low oxygen and very low moisture environments to avoid contamination of the salt with oxygen and moisture.
16. In glove box, remove mold housing seal and load salt into funnel and mold.
17. In glove box, replace mold housing seal and clamp closed. Steps 15-17 are performed in a very low oxygen and very low moisture environment of a glove box to load the appropriate quantity of salt that will fill the internal void of the test specimen to a level above the gage length, and prepare for transport back to the vacuum chamber.

In a subsequent "ingot fabrication" phase, the salt is melted and re-solidified within the mold to remove impurities and voids within the salt. The ingot fabrication phase can include all or some of the following steps:

18. Transport sealed mold housing from glove box to vacuum chamber.
19. With Ar-4% H2 flowing, open vacuum chamber.
20. With Ar-4% H2 flowing, place mold housing into furnace.
21. With Ar-4% H2 flowing, remove mold housing seal and gasket.
22. With Ar-4% H2 flowing, place thermocouple into salt.
23. With Ar-4% H2 flowing, reseal vacuum chamber.
24. Pull high vacuum on chamber.
25. Back fill with Ar-4% H2. Repeat steps 24 and 25 as needed.
26. In flowing Ar-4% H2, heat system, e.g. to 600° C., until salt melts.
27. In flowing Ar-4% H2, cool down to room temperature. This process results in the fabricated ingot of highly purified salt with minimal re-contamination with oxygen and moisture.

In a subsequent "ingot installation" phase, the salt ingot fabricated in the ingot fabrication phase is placed into and sealed within a test specimen while minimizing exposure of the ingot. The ingot installation phase can include all or some of the following steps:

28. With Ar-4% H2 flowing, open vacuum chamber.
29. With Ar-4% H2 flowing, quickly place mold housing seal onto mold housing and clamp closed.
30. With Ar-4% H2 flowing, remove sealed mold housing and reseal vacuum chamber.
31. Transport sealed mold housing to glove box with low moisture and low oxygen atmosphere (e.g., in weld area). Steps 28-31 allow ingot, mold and funnel to be transported without exposure to air and moisture.
32. In glove box, remove mold housing seal and remove salt ingot from mold.
33. In glove box, load salt ingot into test specimen void.
34. In glove box, add end plug to test specimen to seal ingot within specimen.
35. In glove box, weld end plug in place. This allows the specimen to be tested without exposing the salt to oxygen or moisture.

The above described method for preparing the salt ingot can be used for purified salt that cannot be readily reduced to sufficiently small particles. For salt that when purified can be readily reduced to sufficiently small particles, an alternative method can be used wherein the required quantity of the purified salt is loaded directly into the specimen in a very low oxygen, very low moisture glove box.

Exemplary Testing Procedures

The following describes an exemplary procedure for preparing an exemplary stress-rupture testing system and test specimen, such as described herein, and testing the test specimen with a salt ingot sealed within the specimen, as described herein. Preparing and using the testing system can include all or some of the following steps:

1. Apply boron nitride to threads on upper and lower ends of the test specimen to prevent seizing up after long exposure to high testing temperature under load, assemble the basin ring to the specimen below the gage portion, and then install the specimen into the load train.
2. Install three thermocouples at the top, middle, and bottom of the specimen gage portion.
3. Install a salt leak indicator cable, such as along the upper pull rod, and fix an indicator tip of the cable to the basin ring.
4. Install the thermal break assembly on bottom of the load train.
5. Test thermocouples to make sure they all work properly.
6. Clean the load train, such as with alcohol, to remove impurities that may generate contaminating gases at high testing temperature inside the environmental chamber. Place insulation cloth around the pull rod above the thermal break adaptor, and insert the load train into the environmental vessel.
7. Install the lower cross chamber right flange with the cooling coil around the thermal break lower pull rod inside the lower cross chamber.
8. Install the load cell onto the lower pull rod below the bottom of the thermal break.

9. Connect the load cell signal leads to its inlet cable on the left flange of the lower cross chamber and then install the left flange to the lower cross chamber.

10. Screw the bottom pull rod into the load cell while holding the load cell.

11. Attach the bottom end flange to the lower cross chamber and orientate so the inert gas line easily connects to the bottom end flange.

12. Tighten down all flanges.

13. Connect all gas lines.

14. Connect outside load cell cable to its inlet adaptor on the left flange.

15. Connect the three thermocouples and the salt leak indicator to the top of the vessel.

16. Connect water cooling lines on top pull rod, bottom pull rod, and right flange.

17. Attach load train to loading source, such as a creep machine.

18. Flush the vessel with purified argon flowing in from the bottom and out from the top. Because argon is heavier than oxygen and nitrogen, which are the major elements in air, the argon atmosphere that builds from the bottom gradually pushes the air up and out through the top gas line outlet.

19. The argon flow rate is set to fill the vessel in approximately 45 minutes. After approximately 180 minutes, which allows argon 3-4 times of the vessel volume to flush through the vessel, the system is ready for temperature increase.

20. Turn on the salt leak indicator.

21. Turn on the recirculation water system to start the cooling water flow.

22. Start the furnace and slowly raise the furnace temperature to the prescribed testing temperature.

23. When the prescribed temperature is stabilized, reset dial gage, add prescribed testing weight to load train, and start the timer. Test starts.

24. Monitor specimen during testing until specimen fails, such as by rupturing at the gage portion.

25. Remove load, decrease temperature, and remove argon and collect salt.

Unless otherwise noted, technical terms are used herein according to conventional usage. In order to facilitate review of the various embodiments of the disclosure, the following explanation of terms is provided.

The singular terms "a", "an", and "the" include plural referents unless context clearly indicates otherwise. The term "comprises" means "includes without limitation." The term "coupled" means directly or indirectly linked and does not exclude intermediate elements between the coupled elements. The term "and/or" means any one or more of the elements listed. For example, the term "A and/or B" means "A", "B" or "A and B."

Although methods and materials similar or equivalent to those described herein can be used in the practice or testing of the present technology, only certain suitable methods and materials are described herein. In case of conflict, the present specification, including terms, will control. For purposes of this description, certain aspects, advantages, and novel features of the embodiments of this disclosure are described. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

Unless otherwise indicated, all numbers expressing properties, sizes, percentages, measurements, distances, ratios, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, numbers are not approximations unless the word "about" is recited.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of the following claims.

The invention claimed is:

1. A system for stress-rupture testing of materials in a high-temperature liquid salt environment, the system comprising:

a vertically elongated vessel having an upper end and a lower end, the vessel comprising one or more gas ports for maintaining a controlled inert gas environment within the vessel;

a first pull rod positioned within the vessel and extending downwardly from or through the upper end of the vessel, the first pull rod having a first specimen grip at a lower end of the first pull rod, the first specimen grip adapted to grip an upper end of a test specimen having a tubular gage portion for containing a salt;

a second pull rod positioned within the vessel below the first pull rod, the second pull rod having a second specimen grip at an upper end of the second pull rod, the second specimen grip adapted to grip a lower end of the test specimen;

a thermal break positioned within the vessel and coupled to a lower end of the second pull rod, the thermal break comprising a fixture coupled to a lower end of the second pull rod and a thermally insulating spacer supported by the fixture below the second pull rod; and a third pull rod having an upper end spaced below the lower end of the second pull rod and spaced within the thermal break fixture, the upper end of the third pull rod being supported by the thermally insulating spacer such that the third pull rod is thermally decoupled from the second pull rod by the thermally insulating spacer, the third pull rod having a lower end that extends through a lower end of the vessel and is adapted to be coupled to a loading source for applying a load to the test specimen via the second and third pull rods and the thermal break.

2. The system of claim 1, further comprising a load cell coupled to the third pull rod within the vessel below the thermal break, the load cell being thermally protected by the thermal break and configured to measure the load applied to the test specimen via the third pull rod.

3. The system of claim 1, further comprising a furnace positioned around an upper portion of the vessel for maintaining the test specimen at a desired temperature that is sufficient to cause a salt within the test specimen to be in the liquid phase.

4. The system of claim 1, wherein the thermal break fixture comprises a metallic tubular body having an upper end secured to the second pull rod and a lower end forming an inner ledge that supports a lower surface of the thermally insulating spacer.

5. The system of claim 4, wherein the thermally insulating spacer comprises a ceramic disk and the upper end of the third pull rod comprises a flared head that contacts an upper surface of the ceramic disk and is spaced apart from the fixture and the second pull rod.

6. The system of claim 1, wherein the vessel comprises a lower opening through which the third pull rod extends, there being a gap between the third pull rod and the lower opening such that inert process gas from within the vessel is allowed to exit the vessel through the gap.

7. The system of claim 1, further comprising a cooling coil coupled to the third pull rod within the vessel below the thermal break.

8. The system of claim 1, wherein the system is capable of applying a stress load to the test specimen while the test specimen is maintained at a temperature greater than 700° C.

9. The system of claim 1, wherein the salt comprises $2^7\text{LiF}$—$\text{BeF}_2$ or KF—$\text{ZrF}_4$.

10. A test specimen for stress-rupture testing in a high-temperature liquid salt environment, the test specimen comprising:
    a first end portion having a first engagement portion for connecting to a stress-rupture testing system;
    a second end portion having a second engagement portion for connecting to the stress-rupture testing system;
    a narrowed gage portion between the first and second end portions; and
    an inner void extending through the first end portion and through the gage portion;
    wherein the gage portion has a substantially cylindrical outer surface defining an outer diameter and the inner void is substantially cylindrical within the gage portion such that the gage portion has a substantially cylindrical inner surface defining an inner diameter and the gage portion has a substantially constant wall thickness between the inner diameter and the outer diameter;
    wherein the inner void is configured to receive a salt in solid form such that when the test specimen is subjected to high temperatures, the salt melts to form molten salt that completely fills the portion of the void that is within the gage portion; and
    wherein a ratio Ai/V of the gage portion is at least about 20, wherein Ai is the inner surface area of the gage portion and V is the volume of material in the gage portion between the inner surface of the gage portion and the outer surface of the gage portion, in units of square inches divided by cubic inches.

11. The test specimen of claim 10, wherein the ratio Ai/V of the gage portion is at most about 32.

12. The test specimen of claim 10, wherein the inner diameter is in a range of from about 0.41 inches (about 10.41 mm) to about 0.44 inches (about 11.18 mm).

13. The test specimen of claim 10, further comprising a basin ring that is attached around the test specimen below the gage portion and configured to catch liquid salt that escapes from inside the test specimen when the test specimen ruptures or leaks during stress-rupture testing.

14. A method of stress-rupture testing of a selected material in a high-temperature liquid salt environment, the method comprising:
    placing a solid salt ingot within an inner void of a test specimen of the selected material and sealing the void closed;
    mounting the test specimen, with the salt ingot enclosed, in a load train within a vessel of a stress-rupture testing system;
    filling the vessel with an inert gas;
    heating the test specimen, while mounted in the load train within the vessel filled with inert gas, such that the salt ingot melts within the void and the resulting molten salt contacts an entire inner surface of a gage portion of the test specimen;
    applying a load to the gage portion of the test specimen while the test specimen is mounted in the load train within the vessel filled with inert gas and the salt is molten, and measuring the applied load until the gage portion of the test specimen fails.

15. The method of claim 14, wherein the method further comprises continuously feeding the inert gas into the vessel while the load is applied and allowing the inert gas to escape from the vessel through a gap between the load train and a lower end of the vessel.

16. The method of claim 14, wherein heating the test specimen comprising heating the test specimen to a temperature that is at least 100 degrees C. greater than the melting temperature of the salt.

17. The method of claim 14, wherein measuring the applied load is performed at least in part by a load cell mounted within the load train positioned within the vessel.

18. The method of claim 14, wherein placing the solid salt ingot within an inner void of a test specimen comprises:
    placing a mold within a vacuum chamber;
    creating an inert gas environment within the vacuum chamber around the mold;
    heating the mold within the vacuum chamber in the inert environment to remove impurities from the mold;
    after removing impurities from the mold, placing a salt into the mold and closing the mold in an inert environment;
    heating the mold to melt the salt and remove voids and impurities from the salt;
    cooling the mold to solidify the salt into the salt ingot with impurities removed; and
    transferring the salt ingot from the mold into a test specimen in an inert environment.

19. The method of claim 18, wherein creating an inert gas environment within the vacuum chamber comprises drawing a vacuum on the vacuum chamber and feeding an inert gas into the vacuum chamber to purge ambient air from the vacuum chamber.

20. The method of claim 18, wherein the method further comprises:
    placing a funnel and a mold housing within a vacuum chamber along with the mold;
    heating the mold, funnel, and mold housing within the vacuum chamber in the inert environment to remove impurities from the mold, funnel, and mold housing;
    transporting the mold and funnel sealed within the mold housing from the vacuum chamber to a salt-filling chamber having an inert environment;
    using the funnel to place the salt into the mold in the salt-filling chamber; and transporting the salt-filled mold sealed within the mold housing from the salt-filling chamber to a vacuum chamber.

* * * * *